(12) United States Patent
Baumgart

(10) Patent No.: US 6,383,185 B1
(45) Date of Patent: May 7, 2002

(54) MEDULLARY NAIL FOR THE DISTRACTION OF BONES

(76) Inventor: Rainer Baumgart, Schieggstrasse 26, 81479 Muenchen (DE)

( * ) Notice: Subject to any disclaimer, the term of this patent is extended or adjusted under 35 U.S.C. 154(b) by 0 days.

(21) Appl. No.: 09/517,007

(22) Filed: Feb. 28, 2000

(30) Foreign Application Priority Data

Mar. 1, 1999  (DE) .......................................... 199 08 851

(51) Int. Cl.[7] .............................................. A61B 17/78
(52) U.S. Cl. .......................................... 606/63; 606/67
(58) Field of Search ............................. 606/67, 68, 62, 606/63

(56) References Cited

U.S. PATENT DOCUMENTS

| | | | | |
|---|---|---|---|---|
| 5,415,660 A | * | 5/1995 | Campbell et al. | 606/62 |
| 5,626,581 A | * | 5/1997 | Staehlin et al. | 606/68 |
| 5,704,939 A | * | 1/1998 | Justin et al. | 606/63 |
| 5,855,579 A | * | 1/1999 | James et al. | 606/67 |
| 5,961,553 A | * | 10/1999 | Coty et al. | 606/62 |
| 5,971,986 A | * | 10/1999 | Santori et al. | 606/63 |
| 6,120,504 A | * | 9/2000 | Brumback et al. | 606/63 |

FOREIGN PATENT DOCUMENTS

| | | |
|---|---|---|
| DE | 39 21 972 C2 | 1/1991 |
| DE | 197 00 225 A1 | 7/1996 |
| EP | 0 320 621 B1 | 11/1988 |

* cited by examiner

Primary Examiner—Paul J. Hirsch
(74) Attorney, Agent, or Firm—Rothwell, Figg, Ernst & Manbeck p.c.

(57) ABSTRACT

The medullary nail (10) for bone distraction has an electric motor drive (20) that is located in its interior (11), preferably in its interior (11) in the area of its tip (12), and is connected with a reception antenna (32) for feeding energy via an electrical connection (31). The reception antenna (32) and the electrical connection (31) are located entirely in the interior (11) of the medullary nail (10). The medullary nail (10) is equipped with an orifice (14), which faces the reception antenna (32) and allows the feeding of energy.

20 Claims, 3 Drawing Sheets

MEDULLARY NAIL FOR THE DISTRACTION OF BONES

BACKGROUND OF THE INVENTION

1. Field of the Invention

The invention concerns a medullary nail (sometimes referred to as a marrow nail) for bone distraction with an electric motor drive arranged in its interior, preferably in its interior in the area of its drive-end, with the electric motor drive being connected to a reception antenna for feeding energy via an electrical connection.

2. Description of the Background Art

From DE 39 21 972 C2 and DE 197 00 225 A1, we are familiar with the utilization of a medullary nail that can be inserted into the bone medullary area as an active implant for the purpose of simultaneous stabilization and distraction of surgically separated hollow bones, particularly in order to extend bones and bridge bone defects. DE 39 21 972 C2 mentions mechanical, pneumatic, hydraulic, electric, electromagnetic and piezo-electric drives in general as power sources that are located in the medullary nail's interior.

According to DE 197 00 225 A1, the planetary roller spindle system known from EP 0 320 621 is considered beneficial.

In both drive systems energy is fed from the outside through the skin via an antenna, which is connected with the drive in the medullary nail's interior via a cable.

Furthermore we know of a distraction device which incorporates not only the drive, but also all energy reserves and controls in a capsule so that the system works completely autonomously and must be accessed from the outside only for programming purposes.

The cable connection between the antenna and the drive system represents a highly stressed component. The medullary nail on the femur (thigh bone) is inserted between the greater trochanter and the neck of the femur. This is also where the cable exits and leads to the antenna, which is usually located subcutaneously. With every movement of the leg, the cable exit area performs a circular segment motion with the turning center of the hip joint, which exposes the cable at the exit area out of the bone to a bending stress with very small bending radius, in particular since ossifications also occur in this area on a regular basis. Even when employing highly flexible cables, such as those common in pacemakers, durability cannot be guaranteed with certainty. Problems also arise upon removal of the cable later on, which is sheathed in the tissue by a delicate cover of connective tissue. In case the cable breaks or is damaged during surgery, unsterile material can come in contact with body fluids.

According to DE 39 21 972 C2 (FIG. 1), the distraction device cannot be employed on the tibia since in its proximity a bend in the medulary nail is required for anatomical reasons to ensure that the medullary nail is not pulled into the bone by the distraction process.

In this case, the drive system from DE 197 00 225 A1 (FIG. 2) would be suitable because the drive is located distally of the bend. However even in this case routing of the cable, which leaves the bone immediately before the crucial ligament and runs through the knee cap to the subcutaneously located antenna, is problematic.

If we were to design the drive for the medullary nail as described in DE 39 21 972 D2 in such a way that it would be located distally, then it is true that its function would be ensured since the medullary nail will be able to run proximally. The cable connection to the outside, however, would have to be routed through the nail or next to the nail on its outside, which would be very complex from a technical point of view.

On the version mentioned above where not only the drive, but also all energy reserves and controls are encapsulated, the cable routing problem has been eliminated through the complete integration of all components into the medullary nail's interior. Energy resources, however, are limited and the system is prone to failures; furthermore, there is the risk that the system may become independent.

In summary, this shows that considerable disadvantages arise from known drive systems, not only with a cable connection routed freely through body tissue between the components in the nail's interior and the antenna, which is generally located subcutaneously, but also with complete implantation of all components, including the energy supply, into the medullary nail's interior.

SUMMARY OF THE INVENTION

The object of the invention comprises designing medullary nails of the kind described above in such a way that an energy feeding system is guaranteed both on the femur and the tibia—while maintaining distraction under tension in accordance with DE 39 21 972 C2 or while maintaining the telescope mechanism in accordance with DE 197 00 225 A1—which avoids both the disadvantages of a complete integration of energy reserves into the encapsulated system and those of a cable connection to a subcutaneously located reception system.

Based on medullary nails of the kind described above, this object is arrived at by locating the reception antenna and electrical connection either entirely in the interior of the medullary nail and equipping the medullary nail with an orifice that faces the reception antenna and permits the feeding of energy, or immediately on the front so that energetic shielding cannot occur from the metal of the medullary nail.

On the invented medullary nail, all cable connections outside the medullary nail are eliminated. At the same time, the required feeding energy system is made possible with the help of a high frequency transmitter, which can transmit the required energy without difficulty when positioned in appropriate proximity. This design always makes the desired energy resources, which are required for the drive, available without having to install them as such within the medullary nail. The orifice can be closed off in a wall-like manner with a material that allows the feeding of energy so that the medullary nail has a consistently even outline.

The orifice can be located in the wall of the medullary nail. If in this version the drive, the reception antenna and its electrical connection, usually a cable or plug-type connector, were arranged in the same housing, then it would be inserted into the medullary nail's interior in such a way that one orifice of the joint housing facing the reception antenna would be opposite the orifice in the wall of the medullary nail. This enables pre-assembly of the drive, reception antenna and electrical connection in the joint housing without this joint housing representing a shield that would impair the energy feeding process. The orifice in the joint housing can certainly also be closed off by a material that permits the feeding of energy so that the joint housing has a flush outer wall or is connected with the material, which permits the feeding of energy, in the orifice of the medullary nail's wall without joints. The joint housing can consist of metal.

Generally, an epoxy resin or silicone rubber that is tolerated by the body is utilized as the material that allows the feeding of energy.

At least the reception antenna, and usually its electrical connection as well, can be enclosed by a casing-like encapsulation made of material that allows the feeding of energy, with the possibility of the encapsulation being firmly connected to the electric motor drive and inserted into the medullary nail's interior with or without drive.

In order to enable true alignment of the reception antenna and the orifices, adjusting elements can be provided for on the medullary nail and the housing or the encapsulation, e.g. in a recess extending distally from the tip of the medullary nail and a lug protruding radially from the housing or encapsulation. Similarly, the adjusting elements can consist of the orifice in the wall of the medullary nail and a neck that protrudes from the circumferential area of the encapsulation in alignment with the reception antenna and snaps into the orifice in a form-fit way, if this neck, like the encapsulation, is made of elastic silicone rubber.

In a special design the orifice can extend distally in axial direction over the entire circumferential area of the medullary nail, starting from its tip. In this case the encapsulation protrudes proximally beyond the material that allows the feeding of energy and axially beyond the medullary nail, and forms a cap that encloses the reception antenna.

In all cases that have been mentioned, it is possible to attach a suitable tool to the medullary nail on the front in order to be able to place the medullary nail into the bone and remove it again.

BRIEF DESCRIPTION OF THE DRAWINGS

The versions of this invention are explained more in detail with the help of drawings. They show.

DETAILED DESCRIPTION OF THE INVENTION

Figure 1:
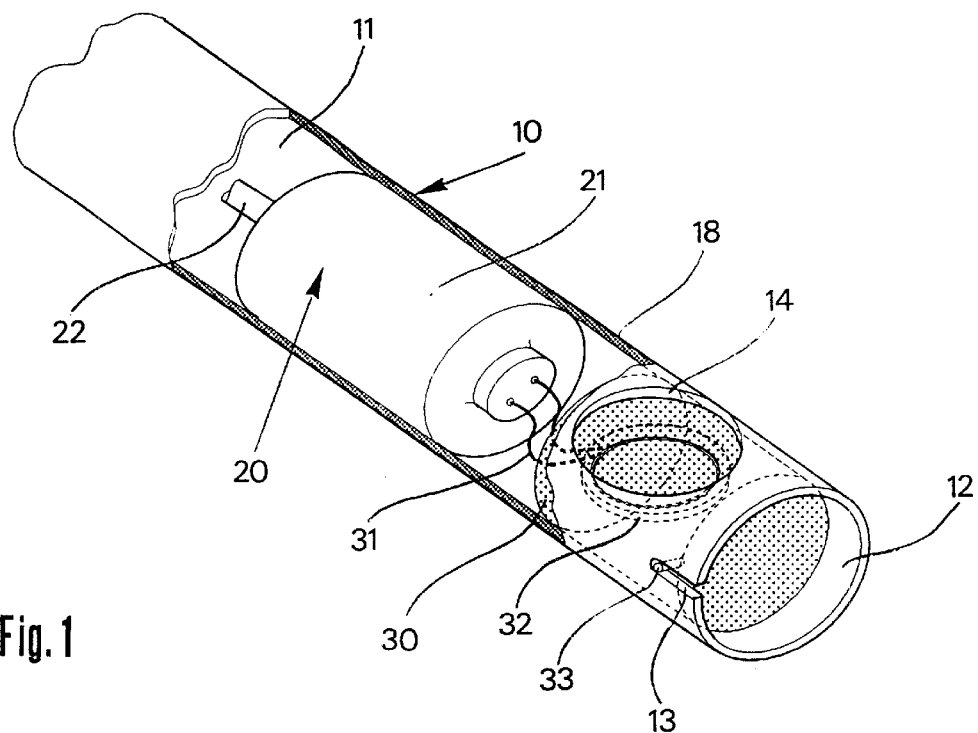
FIG. 1 perspective view of the tip in a first version of a medullary nail.

FIGS. 1 through 5, respectively, only show the area of the tip 12 of a medullary nail 10 with a drive 20. The design of the distraction mechanism of the medullary nail 10 corresponds to the examples described in DE 39 21 972 C2 or DE 197 00 225 A1.

The medullary nail 10, which comprises of metal, has an elongated, basically cylindrical shape with a wall 18, which can be open or closed on the tip 12. The hollow interior 11 of the medullary nail 10 is equipped with an electric motor drive 20, which is encapsulated into a drive housing 21 and can be connected to the distraction mechanism (not shown) via a drive shaft 22. Furthermore, the drive 20 is connected with a reception antenna 32, located in a casing-like encapsulation 30, via an electrical connection, which is shown as a cable 31, with the antenna 32 being located in the drive-end side of the medullary nail 10 opposite a window-like orifice 14 in the wall 18 of the medullary nail 10.

In order to ensure that the reception antenna 32 is actually located opposite the orifice 14, the wall 18 is equipped—on the tip 12 of the medullary nail 10—with a recess 13 that is open towards the front and into which a lug 33 of the casing-like encapsulation 30 of the reception antenna 32 snaps in a form-fit manner.

The energy that is required for the respective adjustments of the distraction mechanism of the medullary nail 10 is transmitted by a transmitter (not shown) via the orifice 14, which is basically free from metals, to the reception antenna 32, which converts received energy as required by appropriate electronic components and feeds it to the electric motor drive 20 via the cable 31. Since the electric connection in the form of the cable 31 is located inside the medullary nail 10, i.e. no cable has to be provided for outside the medullary nail 10, the medullary nail can be employed without difficulty both on the femur and on the tibia.

Figure 2:
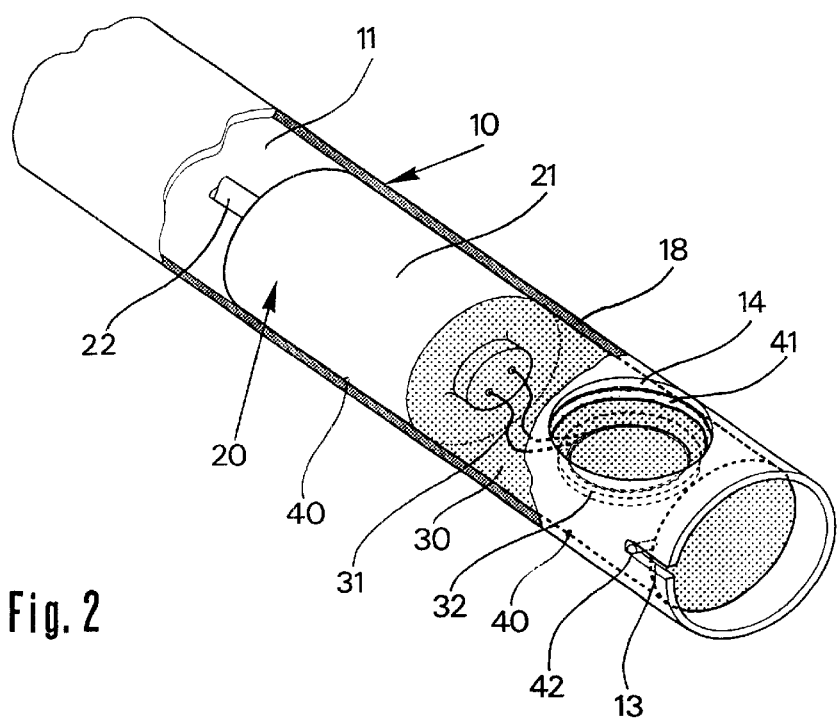
FIG. 2 perspective view as in FIG. 1 of the tip of a second version of the medullary nail.

In the design in FIG. 2 the electric motor drive 20, the electrical connection in the form of a cable 31 and the reception antenna 32 are arranged in a joint metal housing 40 that is equipped with a window-like orifice 40. This capsule-like design is either connected with the distraction mechanism with the drive shaft 22 protruding from it by inserting it into the interior 11 of the medullary nail 10 or already has a firm connection with the distraction mechanism before insertion into the medullary nail, in which case the final position of the orifice 41 of the joint housing 40 is aligned with the orifice 14 in the wall 18 of the medullary nail 10 in such a way that the feeding of energy for the reception antenna 32 can occur through the orifices 14 and 41 without impairment by a metallic shield. The orifice 41 can be sealed off with a material that allows the feeding of energy, e.g. an epoxy resin or silicone rubber that is tolerated by the body. In order to ensure that the final position of the orifice 41 in the housing 40 is truly aligned with the orifice 14 in the wall 18 of the medullary nail 10, a lug 42 of the housing 40 can be incorporated into a recess 13 in the wall 18, starting from the proximal front of the medullary nail 10.

Figure 3:
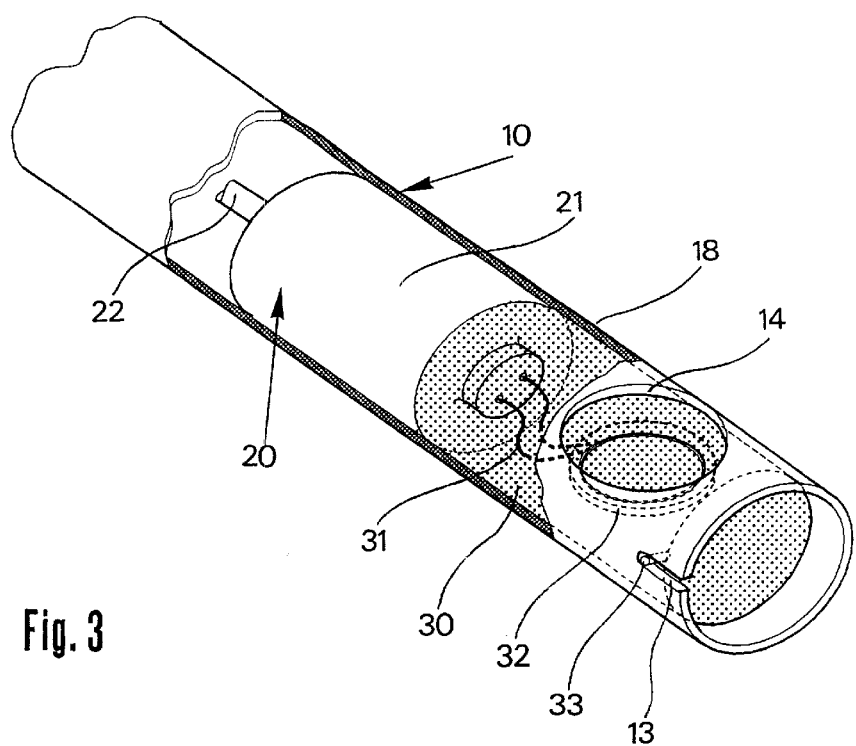
FIG. 3 perspective view as in FIG. 1 of the tip of a third version of the medullary nail and FIG. 4 perspective view like in FIG. 1 of the tip of a fourth version of the medullary nail.

In the design in FIG. 3, the electric motor drive 20, the electrical connection in the form of a cable 31 and the reception antenna 32 represent a unit by encapsulating the cable 31 and the reception antenna 32 into epoxy resin or silicone rubber, with the casing-like encapsulation 30 formed this way having a firm connection with the electric motor drive 20. In this case as well, a recess 13 in the medullary nail 10 and a lug 33 in the encapsulation 30 ensure that the reception antenna 32 and the orifice 14 of the medullary nail 10 are aligned.

Figure 4:
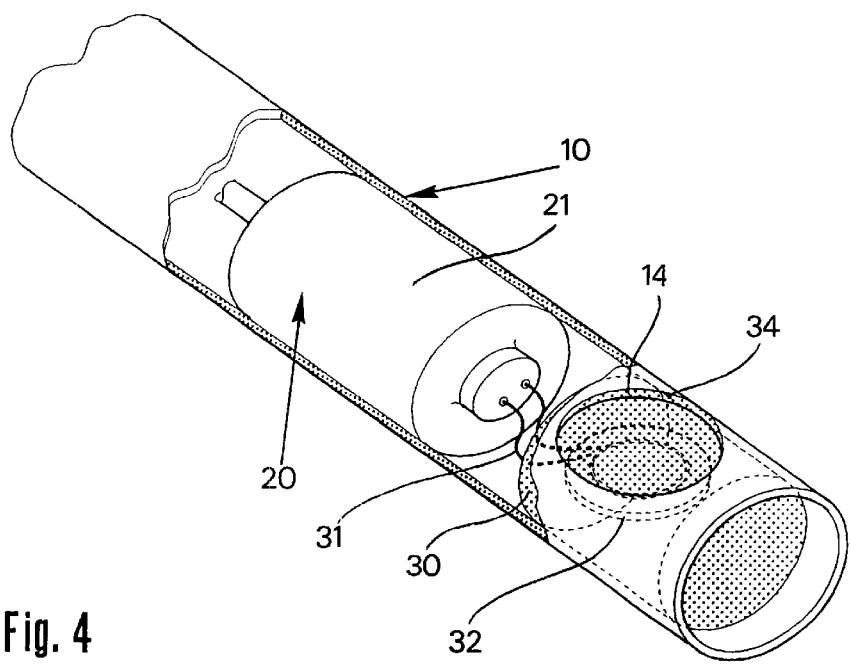

In the design in FIG. 4, the encapsulation 30 for the cable 31 and the reception antenna 32 are made of flexible silicone rubber and equipped with a neck 34, which protrudes from the encapsulation's circumferential area as the radial extension of the embedded reception antenna 32, whose shape corresponds to that of the orifice 14, and which can "snap-fit" into the orifice 14 of the medullary nail 10. This ensures that the reception antenna 32 is truly aligned with the housing orifice 14.

Figure 5:
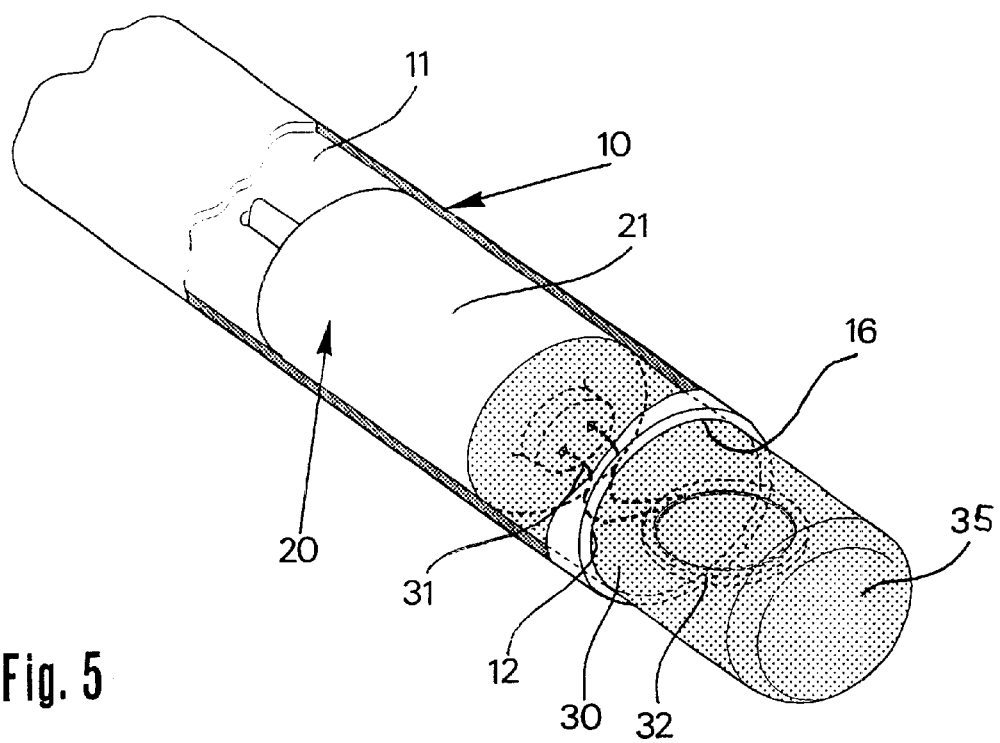
FIG. 5 perspective view like in FIG. 1 of the tip of a fifth version of the medullary nail.

The version in FIG. 5 employs the orifice 16 on the front of the medullary nail 10 as opening for feeding energy. Here the electric motor drive 20 is firmly connected with a casing-like encapsulation 30, which is introduced into the interior 11 of the medullary nail 10 from the tip 12 of the medullary nail 10 and into which the reception antenna 32 as well as the electrical connection, in the form of a cable 31 routed from the reception antenna 32 to the electric motor drive 21, are embedded. The encapsulation 30 made of epoxy resin or silicone rubber protrudes from the front orifice 16 in the form of a cap 35, which encloses the reception antenna 32, so that in this case the orifice 14 can be interpreted as one that extends across the entire circumferential area of the medullary nail 10.

REFERENCE LIST

10 Medullary Nail
11 Interior
12 Tip
13 Recess
14 Orifice
16 Orifice (Front)
18 Wall
20 Drive
21 Drive Housing
22 Drive Shaft
30 Encapsulation
31 Cable
32 Reception Antenna
33 Lug
34 Neck
35 Cap
40 Housing (Metal)
41 Orifice
42 Lug

What is claimed is:

1. A medullary nail for bone distraction, said medullary nail comprising:
    an orifice;
    an interior enclosed by said medullary nail;
    an electric motor drive located in said interior;
    a reception antenna located in said interior for feeding energy required by said electric drive motor; and
    an electrical connection in said interior connecting said electric motor drive and said reception antenna;
    wherein the orifice faces the reception antenna and permits the feeding of energy.

2. The medullary nail according to claim 1, wherein the orifice is sealed with a first material that permits the feeding of energy.

3. The medullary nail according to claim 1, comprising further a wall; and
    wherein said orifice is a wall orifice; and
    the wall orifice is located in said wall.

4. The medullary nail according to claim 3, comprising further:
    a joint housing, said joint housing being located in the interior, said joint housing having a joint housing orifice;
    the reception antenna and said electrical connection being located in said joint housing; and
    wherein said reception antenna faces said joint housing orifice; and
    the joint housing orifice is located opposite the wall orifice.

5. The medullary nail according to claim 4, wherein the joint housing is made of metal.

6. The medullary nail according to claim 4, wherein the joint housing orifice is closed with a second material that allows the feeding of energy.

7. The medullary nail according to claim 1, comprising further:
    a casing, said casing being inserted in said interior;
    the reception antenna being enclosed by said casing; and wherein:
    said casing is made of a third material that allows the feeding of energy.

8. The medullary nail according to claim 7, wherein:
    the reception antenna is enclosed by said casing;
    said electrical connection is enclosed by said casing; and
    the casing has a firm connection with the electric motor drive.

9. The medullary nail according to claim 4, comprising further:
    a wall adjusting element on the medullary nail;
    a joint housing adjusting element on the joint housing; and
    wherein said wall adjusting element and said joint housing adjusting element enable true alignment of the reception antenna and the wall orifice.

10. The medullary nail according to claim 9, wherein said medullary nail comprises further a tip; and
    wherein the wall adjusting element comprises a recess that extends distally from the tip; and
    the joint housing adjusting element comprises a lug that protrudes radially from the housing.

11. The medullary nail according to claim 9, wherein the wall adjusting element comprises the wall orifice; and
    said joint housing element comprises a silicone rubber neck that protrudes from a circumferential area of the joint housing in alignment with the reception antenna and snaps into the wall orifice in a form-fit manner.

12. The medullary nail according to claim 8, wherein the casing protrudes axially beyond the medullary nail and encloses the reception antenna.

13. The medullary nail according to claim 1, wherein the first material is selected from the group consisting of:
    epoxy resin, or silicone rubber.

14. The medullary nail according to claim 1, wherein said medullary nail comprises further a tip; and
    said electric motor drive is located in said tip.

15. The medullary nail according to claim 7, comprising further:
    a wall adjusting element on the medullary nail;
    a casing adjusting element on the casing; and
    wherein said wall adjusting element and said casing adjusting element enable true alignment of the reception antenna and the wall orifice.

16. The medullary nail according to claim 15, wherein said medullary nail comprises further a tip; and
    wherein the wall adjusting element comprises a recess that extends distally from the tip;
    and the casing adjusting element comprises a lug that protrudes radially from the casing.

17. The medullary nail according to claim 7, wherein:
    said casing has a casing orifice;
    the reception antenna and said electrical connection being located in said casing; and wherein:
    said reception antenna faces said casing orifice; and
    the casing orifice is located opposite the wall orifice.

18. The medullary nail according to claim 7, comprising further:
    a wall adjusting element on the medullary nail;
    a casing adjusting element on the casing; and
    wherein said wall adjusting element and said casing adjusting element enable true alignment of the reception antenna and the wall orifice.

19. The medullary nail according to claim 18, wherein said medullary nail comprises further a tip; and wherein the wall adjusting element comprises a recess that extends distally from the tip; and the casing adjusting element comprises a lug that protrudes radially from the casing.

20. The medullary nail according to claim 18, wherein the wall adjusting element comprises the wall orifice; and said casing element comprises a silicone rubber neck that protrudes from a circumferential area of the casing in alignment with the reception antenna and snaps into the wall orifice in a form-fit manner.

* * * * *